Figure 3:
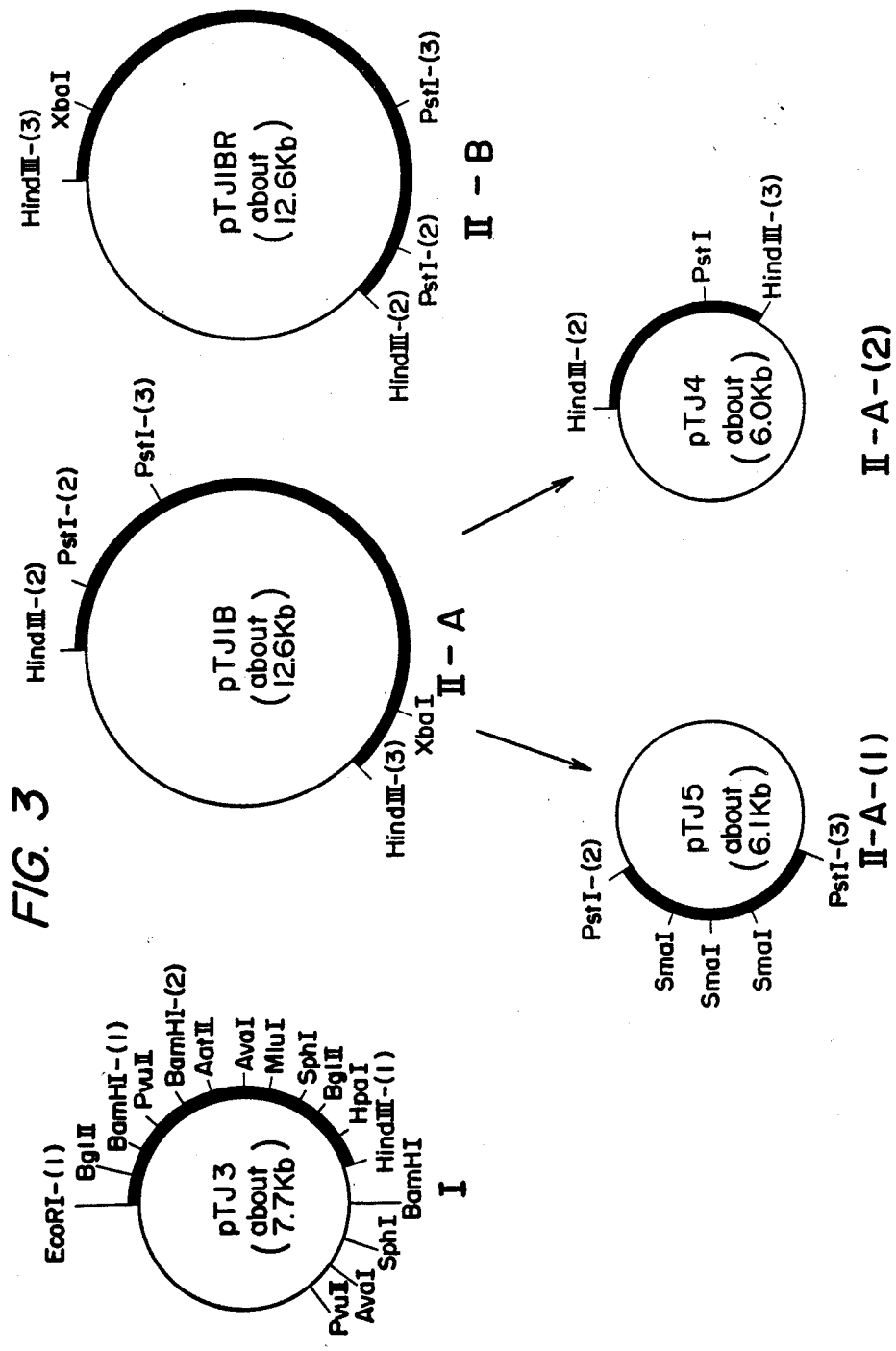

United States Patent [19]

Kudo et al.

[11] Patent Number: 4,935,496

[45] Date of Patent: Jun. 19, 1990

[54] MOUSE-HUMAN CHIMAERIC IMMUNOGLOBULIN HEAVY CHAIN SPECIFIC FOR THE CALL ANTIGEN

[75] Inventors: Akira Kudo; Yushi Nishimura, both of Fukuoka; Yataro Ichikawa, Tokorozawa; Takeshi Watanabe, Saga, all of Japan

[73] Assignee: Teijin Limited, Osaka, Japan

[21] Appl. No.: 805,381

[22] Filed: Dec. 4, 1985

[30] Foreign Application Priority Data

Dec. 4, 1984 [JP] Japan .................................. 59-254980

[51] Int. Cl.⁵ ...................... C07K 13/00; C07K 15/04; A61K 39/395
[52] U.S. Cl. .................................. 530/388; 530/387; 530/808; 530/809; 530/828; 435/172.3; 435/172.2; 935/15
[58] Field of Search .................. 530/387, 388; 424/85; 435/68, 172.3, 172.2, 290.2

[56] References Cited

U.S. PATENT DOCUMENTS 4,645,738 2/1987 Knowles et al. .................. 435/7
4,731,244 3/1988 Talle et al. ........................ 424/87

FOREIGN PATENT DOCUMENTS 0125023 11/1984 European Pat. Off. .

OTHER PUBLICATIONS

Neuberger et al., Nature, 312, 604–618, Dec. 13, 1984.
Marx, Science, 229, 455–446, Aug. 2, 1985.
Sharon et al., Nature, 309, 364–377, May 24, 1984.
Morrison, Science, 229, 1202–1207, Sep. 20, 1985.
Morrison et al., PNAS, 81, G 851–855, Nov. 1984.
Takeda et al., Nature, 314, 452–454, Apr. 4, 1985.
Deng et al., Blood, 61(4), 759–769, Apr. 1983.
Bakri et al., Cancer 54(2), 284–292, Jul. 15, 1984.
Munro, Nature, 312, 597, Dec. 13, 1984.
Oi et al., PNAS, 80, 825–829, 1983.
Roitt et al. (EDs.), in "Immunology", Chapter 5, pp. 5.1 to 5.9, 1985 pub. date.
Gillies et al., Cell, 33, 717–728, 1983. (Jul.).
Ochi et al., PNAS, 80, 6351–6355, 1983.
Ueda et al., Proc. Natl. Acad. Sci. USA vol. 79, pp. 4386–4390 Jul. 1982.
Boulianne et al., Nature, Vol. 312, pp. 643–646 (1984).
Neuberger et al., Nature, Vol. 314, pp. 268–270 (1985).

*Primary Examiner*—Margaret Moskowitz
*Assistant Examiner*—Jeff Kushan
*Attorney, Agent, or Firm*—Wenderoth, Lind & Ponack

[57] ABSTRACT

A mouse-human chimaeric immunoglobulin heavy chain comprising (a) the amino acid sequence of a mouse immunoglobulin heavy chain variable region and (b) the amino acid sequence of a human immunoglobulin heavy chain constant region and reacting specifically with human common acute lymphocytic leukemia antigen and a chimaeric DNA fragment which encodes the amino acid sequence of the above mouse-human chimaeric immunoglobulin heavy chain.

1 Claim, 11 Drawing Sheets

FIG. 1-(1)

```
Asp Val Gln Leu Val Glu Ser Gly Gly Gly Leu Val
Gln Pro Gly Gly Ser Arg Lys Leu Ser Cys Ala Ala
Ser Gly Phe Thr Phe Ser Ser Phe Gly Met His Trp
Val Arg Gln Ala Pro Glu Lys Gly Leu Glu Trp Val
Als Tyr Ile Ser Gly Gly Ser Tyr Thr Ile Tyr Tyr
Ala Asp Thr Val Lys Gly Arg Phe Thr Ile Ser Arg
Asp Asn Pro Lys Asn Thr Leu Phe Leu Gln Met Thr
Ser Leu Arg Ser Glu Asp Thr Ala Met Tyr Tyr Cys
Ala Ser Ser Tyr Gly Asn Phe Trp Tyr Phe Asp Val
Trp Gly Ala Gly Thr Thr Val Thr Val Ser Ser Ser
Tyr Gly Asn Phe Trp Tyr Phe Asp Val Trp Gly Ala
Gly Thr Thr Val Thr Val Ser Ser Ala Ser Thr Lys
Gly Pro Ser Val Phe Pro Leu Ala Pro Ser Ser Lys
Ser Thr Ser Gly Gly Thr Ala Ala Leu Gly Cys Leu
Val Lys Asp Tyr Phe Pro Glu Pro Val Thr Val Ser
Trp Asn Ser Gly Ala Len Thr Ser Gly Val His Thr
Phe Pro Ala Val Leu Gln Ser Ser Gly Len Tyr Ser
Leu Ser Ser Val Val Thr Val Pro Ser Ser Ser Leu
Gly Thr Gln Thr Tyr Ile Cys Asn Val Asn His Lys
Pro Ser Asn Thr Lys Val Asp Lys
```

FIG. 1-(2)

```
Lys Val Glu Pro Lys Ser Cys Asp Lys Thr His Thr
Cys Pro Pro Cys Pro Ala Pro Glu Leu Leu Gly Gly
Pro Ser Val Phe Leu Phe Pro Pro Lys Pro Lys Asp
Thr Leu MET Ile Ser Arg Thr Pro Glu Val Thr Cys
Val Val Val Asp Val Ser His Glu Asp Pro Glu Val
Lys Phe Asn Trp Tyr Val Asp Gly Val Glu Val His
Asn Ala Lys Thr Lys Pro Arg Glu Glu Gln Tyr Asn
Ser Thr Tyr Arg Val Val Ser Val Leu Thr Val Leu
His Gln Asp Trp Leu Asn Gly Lys Glu Tyr Lys Cys
Lys Val Ser Asn Lys Ala Leu Pro Ala Pro Ile Glu
Lys Thr Ile Ser Lys Ala Lys Gly Gln Pro Arg Glu
Pro Gln Val Tyr Thr Leu Pro Pro Ser Arg Glu Glu
MET Thr Lys Asn Gln Val Ser Leu Thr Cys Leu Val
Lys Gly Phe Tyr Pro Ser Asp Ile Ala Val Glu Trp
Glu Ser Asn Gly Gln Pro Glu Asn Asn Tyr Lys Thr
Thr Pro Pro Val Leu Asp Ser Asp Gly Ser Phe Phe
Leu Tyr Ser Lys Leu Thr Val Asp Lys Ser Arg Trp
Gln Gln Gly Asn Val Phe Ser Cys Ser Val MET His
Glu Ala Leu His Asn His Tyr Thr Gln Lys Ser Leu
Ser Leu Ser Pro Gly Lys
```

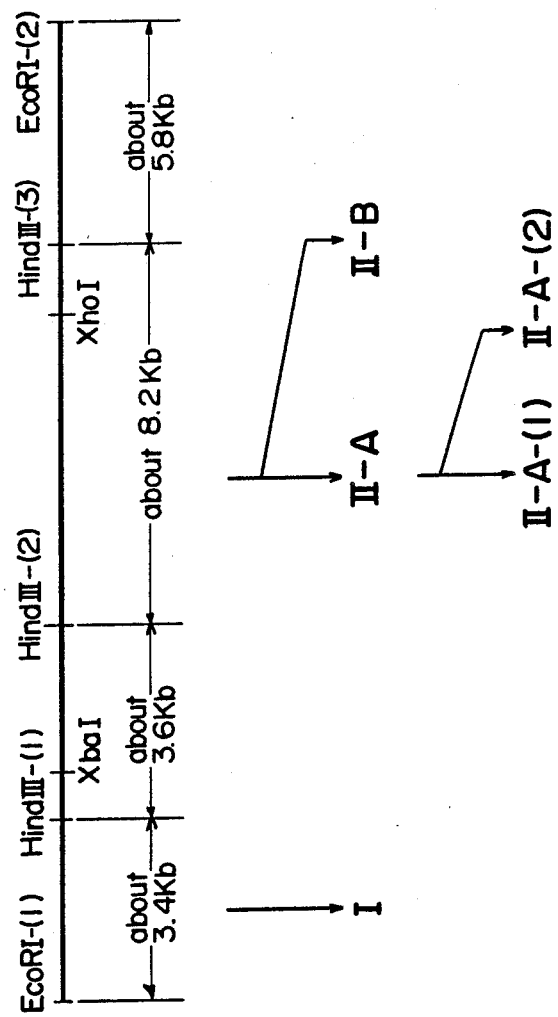

FIG. 4

5'-TTGGCGAGCTGGAAGCAGATGATGAATTAG

AGTCAAGATGGCTGCATGGGGGTCTCCGGC

ACCCACAGCAGGTGGCAGGAAGCAGGTCAC

CGCGAGAGTCTATTTAGGAAGCAAAAAAA

CACAATTGGTAAATTATCACTTCTGGTTG

TGAAGAGGTGGTTTTGCCAGGCCCAGATCT

GAAAGTGCTCTACTGAGCAAAACAACACTT

GGACAATTTGCGTTTCTAAAATAAGGCGAG

GCTGACCGAAATCGAAAGGCTTTTTTTAAC

TATCTGCAATTTCATTTCCAATCTTAGCTT

ATCAACTGCTAGTTGG-3'

FIG. 5-(1)

$C_H1$-segment;

GCCTCCACCAAGGGCCCATCGGTCTTCCCCCTGGCA

CCCTCCTCCAAGAGCACCTCTGGGGGCACAGCGGCC

CTGGGCTGCCTGGTCAGGGACTACTTCCCCGAACCG

GTGACGGTGTCGTGGAACTCAGGCGCCCTGACCAGC

GGCGTGCACACCTTCCCGGCTGTCCTACAGTCCTCA

GGACTCTACTCCCTCAGCAGCGTGGTGACCGTGCCC

TCCAGCAGCTTGGGCACCCAGACCTACATCTGCAAC

GTGAATCACAAGCCCAGCAACACCAAGGTGGACAAG

AAAGTT h-segment;

GAGCCCAAATCTTGTGACAAAACTCACACATGCCCA

CCGTGCCCA

FIG. 5-(2)

$C_H2$-segment;

GCACCTGAACTCCTGGGGGGACCGTCAGTCTTCCTC

TTCCCCCCAAAACCCAAGGACACCCTCATGATCTCC

CGGACCCCTGAGGTCACATGCGTGGTGGTGGACGTG

AGCCACGAAGACCCTGAGGTCAAGTTCAACTGGTAC

GTGGACGGCGTGGAGGTGCATAATGCCAAGACAAAG

CCGCGGGAGGAGCAGTACAACAGCACGTACCGGGTG

GTCAGCGTCCTCACCGTCCTGCACCAGGACTGGCTG

AATGGCAAGGAGTACAAGTGCAAGGTCTCCAACAAA

GCCCTCCCAGCCCCCATCGAGAAAACCATCTCCAAA

GCCAAA $C_H3$-segment;

GGGCAGCCCCGAGAACCACAGGTGTACACCCTGCCC

CCATCCCGGGAGGAGATGACCAAGAACCAGGTCAGC

CTGACCTGCCTGGTCAAAGGCTTCTATCCCAGCGAC

ATCGCCGTGGAGTGGGAGAGCAATGGGCAGCCGGAG

AACAACTACAAGACCACGCCTCCCGTGCTGGACTCC

GACGGCTCCTTCTTCCTCTATAGCAAGCTCACCGTG

GACAAGAGCAGGTGGCAGCAGGGGAACGTCTTCTCA

TGCTCCGTGATGCATGAGGCTCTGCACAACCACTAC

ACGCAGAAGAGCCTCTCCCTGTCCCCGGGTAAA

FIG. 8

```
GATGTGCAGCTGGTGGAGTCTGGGGGAGGCTTAGTGCAGCCT
|←――――――――V-segment――――――――
GGAGGGTCCCGGAAACTCTCCTGTGCAGCCTCTGGATTCACT

TTCAGTAGCTTTGGAATGCACTGGGTTCGTCAGGCTCCAGAG

AAGGGGCTGGAGTGGGTCGCATATATTAGTGGTGGCAGTTAT

ACCATCTACTATGCAGACACAGTGAAGGGCCGATTCACCATC

TCCAGAGACAATCCCAAGAACACCCTGTTCCTACAAATGACC

AGTCTAAGGTCTGAGGACACGGCCATGTATTACTGTGCAAGT

TCCTATGGTAACTTCTGGTACTTCGATGTCTGGGGCGCAGGG

ACCACGGTCACCGTCTCCTCATCCTATGGTAACTTCTGGTAC
――――――――――――――――――→|←―D-segment―→|
TTCGATGTCTGGGGCGCAGGGACCACGGTCACCGTCTCCTCA|
――――――――――J₁-segment――――――――――→
```

MOUSE-HUMAN CHIMAERIC IMMUNOGLOBULIN HEAVY CHAIN SPECIFIC FOR THE CALL ANTIGEN

This invention relates to a mouse-human chimaeric immunoglobulin heavy chain and a chimaeric DNA sequence encoding it. More specifically, it relates to a mouse-human chimaeric immunoglobulin heavy chain comprising a combination of the variable region of a mouse immunoglobulin heavy chain and the constant region of a human immunoglobulin heavy chain, and to a chimaeric DNA sequence encoding it.

Recent studies on immunoglobulin genes have provided much information on the heavy chains ("H-chain" for short) of immunoglobulin genes of mammals, particularly humans. It is well known that generally the H-chain is composed of a variable region which has a site of binding to an antigen and a constant region which has physiological activities such as complement fixation or interaction with particular cells (see "Gendai Kagaku" (Modern Chemistry), November 1981, pages 62–68, published by Baifukan, Tokyo).

On the other hand, the DNA sequences of mouse immunoglobulin genes and their functions have been considerably elucidated. It is now known that a V-segment gene, a D-segment gene and a J-segment gene are aligned in this sequence in the variable region of mouse immunoglobulin genes and a DNA sequence having a promoter function exists upstream of the V-segment gene (5'-terminus). Furthermore, the existence of an enhancer, i.e. a DNA sequence having the function of greatly increasing transcriptional efficiency, between th J-segment gene and the constant region is presumed. It is said that this enhancer exists downstream of the J gene; when it is of the undifferentiated type, it cannot enhance transcription efficiency because the promoter is remote; but it becomes functionable upon recombination in V-J and V-D-J joinings and gains the function of enhancing the efficiency of transcription from the promoter existing upstream of the V gene.

Recently, Walter Schaffner et al. reported the DNA sequence of an enhancer in mouse immunoglobulin H-chain genes (Cell, Vol. 33, 729–740, July 1983).

Susumu Tonegawa et al. likewise determined the existence of an enhancer in mouse immunoglobulin H-chain genes and its DNA sequence (see Cell, vol. 33, 717–728, July 1983).

David Baltimore et al. reported the existence of an enhancer in the light chains ("L-chain" for short) of mouse immunoglobulin genes and its DNA sequence (see Cell, vol. 33, 741–748, July 1983).

The prior efforts have thus resulted in determining the existence of various gene segments and DNA segments having various functions, such as a promoter and an enhancer, in the variable and constant regions of mouse immunoglobulin H-chain and L-chain genes, and the DNA sequences of some of them.

On the other hand, there have been gradual elucidations of the structures and functions of constituent genes of human immunoglobulin H-chain. But the existence of an enhancer was only presumed, and there was no knowledge of the entire DNA sequence of a human enhancer and DNA segments capable of expressing its function.

Very recently, however, T. H. Rabbitts et al. and S. Tonegawa et al. independently reported the DNA sequence of an enhancer in the H-chain of a human immunoglobulin gene (see Nature, vol. 306, 806–809, 22/2a, December 1983 and Nature vol. 307, 334–340, 26 Jan. 1984).

Research on immunoglobulins has thus reached such an advanced stage, and recently allowed utilization of monoclonal antibodies which are expected to find applications in immunological diagnosis and therapy, for example in the diagnosis, control and prevention of diseases. The use of human immunoglobulins is most suitable in such immunological diagnosis and therapy utilizing such monoclonal antibodies, but human hybridoma techniques have not reached such a stage that human monoclonal antibodies having any required specificities can be easily obtained as in the case of mouse hybridomas. This imposes great restrictions on immunological diagnosis and therapy of human subjects. A method which might overcome this difficulty is to create artificially an antibody which is very similar to a human antibody and is not recognized as a foreign substance within a human body, and utilize this antibody for immunological diagnosis and therapy. As such an immunoglobulin, a chimaeric immunoglobulin composed of the variable regions of a certain mouse immunoglobulin and the constant regions of a human immunoglobulin was proposed very recently (European Patent Application EP 0 125 023 A1).

The present inventors have also worked extensively in this field in order to create a novel chimaeric immunoglobulin which can be applied to the immunological diagnosis and therapy of humans, and have now found a mouse-human chimaeric immunoglobulin heavy chain which specifically reacts with human common acute lymphocytic leukemia antigen (to be referred to as human "cALL" antigen) in combination with a proper immunoglobulin light chain.

According to this invention, there is provided a mouse-human chimaeric immunoglobulin heavy chain comprising (a) the amino acid sequence of a mouse immunoglobulin heavy chain variable region and (b) the amino acid sequence of a human immunoglobulin heavy chain constant region and reacting specifically with human common acute lymphocytic leukemia antigen in combination with a proper immunoglobulin light chain.

Human cALL antigen is an antigen commonly observed in the blood of patients with various types of acute lymphocytic leukemia. A monoclonal antibody which specifically reacts with human cALL antigen but is not recognized as a foreign substance by humans would greatly contribute the immunological diagnosis and therapy of patients with acute lymphocytic leukemia.

The immunoglobulin heavy chain of this invention has been developed to meet such a need. It is characterized by having a chimaeric structure composed of (a) the amino acid sequence of a mouse immunoglobulin heavy chain variable region, and (b) the amino acid sequence of a human immunoglobulin heavy chain constant region, and also characterized immunologically by reacting specifically with human cALL antigen.

The variable region of the mouse immunoglobulin heavy chain, as mentioned hereinabove, consists roughly of a V-segment, a D-segment and a J-segment, and it is the V-segment which is most involved in the recognition of antigens. The D-segment and J-segment exist in various types depending upon their amino acid sequences, and for example, the existence of $J_1$, $J_2$, $J_3$ and $J_4$ in the J-segment is known. The D- and/or J-segment of the mouse H-chain variable region in the present invention is not limited to any particular amino acid sequence but may vary so long as an antibody finally constructed from the H-chain of this invention has the property of specifically reacting with human cALL antigen. Preferably, however, an H-chain variable region derived from a mouse immunoglobulin H-chain reacting specifically with human cALL antigen is suitable as the mouse immunoglobulin H-chain variable region used in this invention. Specific examples of this variable region include a variable region whose V-segment has the following amino acid sequence

| Asp | Val | Gln | Leu | Val | Glu | Ser | Gly | Gly | Gly | Leu | Val |
| Gln | Pro | Gly | Gly | Ser | Arg | Lys | Leu | Ser | Cys | Ala | Ala |
| Ser | Gly | Phe | Thr | Phe | Ser | Ser | Phe | Gly | Met | His | Trp |
| Val | Arg | Gln | Ala | Pro | Glu | Lys | Gly | Leu | Glu | Trp | Val |
| Ala | Tyr | Ile | Ser | Gly | Gly | Ser | Tyr | Thr | Ile | Tyr | Tyr |
| Ala | Asp | Thr | Val | Lys | Gly | Arg | Phe | Thr | Ile | Ser | Arg |
| Asp | Asn | Pro | Lys | Asn | Thr | Leu | Phe | Leu | Gln | Met | Thr |
| Ser | Leu | Arg | Ser | Glu | Asp | Thr | Ala | Met | Tyr | Tyr | Cys |
| Ala | Ser | Ser | Tyr | Gly | Asn | Phe | Trp | Tyr | Phe | Asp | Val |
| Trp | Gly | Ala | Gly | Thr | Thr | Val | Thr | Val | Ser | Ser |   | and more specifically a variable region having the following total amino acid sequence

| Asp | Val | Gln | Leu | Val | Glu | Ser | Gly | Gly | Gly | Leu | Val |
| Gln | Pro | Gly | Gly | Ser | Arg | Lys | Leu | Ser | Cys | Ala | Ala |
| Ser | Gly | Phe | Thr | Phe | Ser | Ser | Phe | Gly | Met | His | Trp |
| Val | Arg | Gln | Ala | Pro | Glu | Lys | Gly | Leu | Glu | Trp | Val |
| Ala | Tyr | Ile | Ser | Gly | Gly | Ser | Tyr | Thr | Ile | Tyr | Tyr |
| Ala | Asp | Thr | Val | Lys | Gly | Arg | Phe | Thr | Ile | Ser | Arg |
| Asp | Asn | Pro | Lys | Asn | Thr | Leu | Phe | Leu | Gln | Met | Thr |
| Ser | Leu | Arg | Ser | Glu | Asp | Thr | Ala | Met | Tyr | Tyr | Cys |
| Ala | Ser | Ser | Tyr | Gly | Asn | Phe | Trp | Tyr | Phe | Asp | Val |
| Trp | Gly | Ala | Gly | Thr | Thr | Val | Thr | Val | Ser | Ser | Ser |
| Tyr | Gly | Asn | Phe | Trp | Tyr | Phe | Asp | Val | Trp | Gly | Ala |
| Gly | Thr | Thr | Val | Thr | Val | Ser | Ser. |   |   |   |   |

In the present applications, the following abbreviations are used for various amino acids.
Gly: glycine
Ala: alanine
Val: valine
Leu: leucine
Ile: isoleucine
Ser: serine
Asp: aspartic acid
Lys: lysine
Arg: arginine
His: histidine
Phe: phenylalanine
Tyr: tyrosine
Thr: threonine
Cys: cysteine
Met: methionine
Glu: glutamic acid
Trp: tryptophan
Pro: proline
Asn: asparagine
Gln: glutamine On the other hand, polypeptides constituting the constant region of the chimaeric immunoglobulin H-chain of this invention may be those derived from the H-chain of any of IgA, IgD, IgE, IgG and IgM which are known as human immunoglobulins (Ig). Generally, those derived from IgG, above all IgG$_1$, are suitable. More specifically, a polypeptide having the following amino acid sequence is preferred.

| Ala | Ser | Thr | Lys | Gly | Pro | Ser | Val | Phe | Pro | Leu | Ala |
| Pro | Ser | Ser | Lys | Ser | Thr | Ser | Gly | Gly | Thr | Ala | Ala |
| Leu | Gly | Gys | Leu | Val | Lys | Asp | Tyr | Phe | Pro | Glu | Pro |
| Val | Thr | Val | Ser | Trp | Asn | Ser | Gly | Ala | Leu | Thr | Ser |
| Gly | Val | His | Thr | Phe | Pro | Ala | Val | Leu | Gln | Ser | Ser |
| Gly | Leu | Tyr | Ser | Leu | Ser | Ser | Val | Val | Thr | Val | Pro |
| Ser | Ser | Ser | Leu | Gly | Thr | Gln | Thr | Tyr | Ile | Cys | Asn |
| Val | Asn | His | Lys | Pro | Ser | Asn | Thr | Lys | Val | Asp | Lys |
| Lys | Val | Glu | Pro | Lys | Ser | Cys | Asp | Lys | Thr | His | Thr |
| Cys | Pro | Pro | Cys | Pro | Ala | Pro | Glu | Leu | Leu | Gly | Gly |
| Pro | Ser | Val | Phe | Leu | Phe | Pro | Pro | Lys | Pro | Lys | Asp |
| Thr | Leu | MET | Ile | Ser | Arg | Thr | Pro | Glu | Val | Thr | Cys |
| Val | Val | Val | Asp | Val | Ser | His | Glu | Asp | Pro | Glu | Val |
| Lys | Phe | Asn | Trp | Tyr | Val | Asp | Gly | Val | Glu | Val | His |
| Asn | Ala | Lys | Thr | Lys | Pro | Arg | Glu | Glu | Gln | Tyr | Asn |
| Ser | Thr | Tyr | Arg | Val | Val | Ser | Val | Leu | Thr | Val | Leu |
| His | Gln | Asp | Trp | Leu | Asn | Gly | Lys | Glu | Tyr | Lys | Cys |
| Lys | Val | Ser | Asn | Lys | Ala | Leu | Pro | Ala | Pro | Ile | Glu |
| Lys | Thr | Ile | Ser | Lys | Ala | Lys | Gly | Gln | Pro | Arg | Glu |
| Pro | Gln | Val | Tyr | Thr | Leu | Pro | Pro | Ser | Arg | Glu | Glu |
| MET | Thr | Lys | Asn | Gln | Val | Ser | Leu | Thr | Cys | Leu | Val |
| Lys | Gly | Phe | Tyr | Pro | Ser | Asp | Ile | Ala | Val | Glu | Trp |
| Glu | Ser | Asn | Gly | Gln | Pro | Glu | Asn | Asn | Tyr | Lys | Thr |
| Thr | Pro | Pro | Val | Leu | Asp | Ser | Asp | Gly | Ser | Phe | Phe |
| Leu | Tyr | Ser | Lys | Leu | Thr | Val | Asp | Lys | Ser | Arg | Trp |

-continued

| Gln | Gln | Gly | Asn | Val | Phe | Ser | Cys | Ser | Val | MET | His |
|-----|-----|-----|-----|-----|-----|-----|-----|-----|-----|-----|-----|
| Glu | Ala | Leu | His | Asn | His | Tyr | Thr | Gln | Lys | Ser | Leu |
| Ser | Leu | Ser | Pro | Gly | Lys. | | | | | | |

One typical mouse-human chimaeric immunoglobulin H-chain provided by this invention has the amino acid sequence shown in FIG. 1 of the accompanying drawings.

The chimaeric immunoglobulin H-chain of this invention can be produced by joining a DNA fragment encoding the amino acid sequence of the mouse immunoglobulin variable region to a DNA fragment encoding the amino acid sequence of the human immunoglobulin constant region to construct a chimaeric DNA fragment capable of expression, inserting the chimaeric fragment into a plasmid vector, and introducing the recombinant plasmid vector into host animal cells to cause the chimaeric DNA fragment to express in the host cells.

The DNA fragment encoding the amino acid sequence of the mouse immunoglobulin variable region can be obtained, for example, by preparing hybridomas by cell fusion between spleen cells taken from a mouse immunized with membrane pieces of human cALL and mouse myeloma cells, and screening the chromosomal DNA of the hybridomas (see, for example, T. Maniatis et al., Molecular Cloning, Cold Spring Harbor Lab., 1982). Specific procedures therefor are described in detail in Examples 9 to 11 given hereinbelow.

On the other hand, the DNA fragment encoding the amino acid sequence of the human immunoglobulin constant region can be obtained by screening the chromosomal DNA of cells producing human immunoglobulins by a conventional method. Specific procedures therefor are described in detail in Examples 1 to 3 given hereinbelow.

Joining of the two DNA fragments described above through a DNA fragment (to be referred to as the "Eh-segment") at least containing a human enhancer gives a chimaeric DNA sequence encoding the mouse-human chimaeric immunoglobulin H-chain. The Eh-segment should at least contain a human enhancer. It may additionally contain a mouse enhancer or other introns derived from a human or mouse.

The chimaeric DNA fragment is inserted into a suitable plasmid vector such as pSV2gpt, pSV2neo and pKSV-10 to prepare a recombinant plasmid vector.

The recombinant plasmid vector so constructed is introduced into E. coli for example. Thereafter, the recombinant plasmid vector is introduced into host animal cells such as mouse myeloma J558L or NS-1 by the protoplast fusion method (see "Men-eki Jikken Sosa Ho" (Operational Methods in Immunological Experiments) XIII, p. 4533, edited by the Japanese Society of Immunology, 1984). By culturing the resulting cells, the desired mouse-human chimaeric immunoglobulin H-chain can be accumulated in, and recovered from, the culture.

The chimaeric H-chain provided by this invention may be combined with a mouse-human chimaeric immunoglobulin light chain prepared, for example, by the same technique as described above to form a complete mouse-human chimaeric immunoglobulin. Such an immunoglobulin is expected to be used in the immunological treatment of cALL by administering it to human cALL patients either alone or in combination with an anticancer agent.

The following Examples more specifically illustrate the construction and expression of a chimaeric DNA sequence encoding the chimaeric H-chain of this invention.

EXAMPLE 1

Isolation of a human chromosomal DNA:

Human cultivated cells ARH77 ($3 \times 10^8$ cells) were crushed by a glass rod and treated with Protease K (a product of Sigma Co.) in the presence of 2% sodium dodecylsulfate (SDS). Then, phenol saturated with 10 mM Tris HCl (pH 8.0)-1 mM EDTA aqueous solution was added. The mixture was centrifuged to separate it into an aqueous layer and a phenol layer. The aqueous layer was dialyzed against 20 mM Tris HCl (pH 7.5)-100 mM NaCl-5 mM EDTA aqueous solution. The dialyzate was treated with Ribonuclease A (a product of Sigma Co.) and after phenol extraction, dialyzed against 10 mM Tris HCl (pH 8.0)-1 mM EDTA aqueous solution to obtain about 1.2 mg of a human chromosomal DNA [see N. Blin and D. W. Stafford, Nucleic Acids Res., 3, 2303 (1976)].

EXAMPLE 2

Preparation of a human gene library:

The human chromosomal DNA (150 micrograms) obtained in Example 1 was partially digested with restriction endonuclease EcoRI (produced by Takara Shuzo Co., Ltd.) in accordance with the method shown in Example 4, and then subjected to sucrose density gradient centrifugation [sucrose 10–40% (wt/vol), 28,000 rpm$\times$15 hours, 20° C.] to obtain 4.3 micrograms of a DNA fragment having a size of 15 Kb to 23 Kb. The DNA fragment (0.8 microgram) was ligated by using T4-DNA ligase (a product of Bethesda Research Laboratory) with Charon 4A vector [see F. R. Blattner, B. G. Williams, A. E. Blechl, K. D. Thompson, H. E. Faber, L. A. Furlong, D. J. Grunward, D. O. Kiefrr, D. O. More, J. W. Schumm, F. L. Sheldon and Smithies, Science, 196, 161 (1977)] to obtain a hybrid DNA in which the human DNA was inserted between the right arm and left arm of Charon 4A vector. The ligating reaction was carried out at 11° C. for 12 hours in 66 mM Tris-HCl (pH 7.6)-6.6 mM MgCl$_2$-10 mM dithiothreitol-1 mM ATP aqueous solution. The resulting hybrid DNA was packaged in vitro. [A. Becker and M. Gold, Proc. Natl. Acad. Sci. U.S., 72, 581 (1975)] to form a human gene library ($1.8 \times 10^6$ PFU/$\mu$g-DNA, containing more than 99% of human chromosomal DNA).

EXAMPLE 3

Screening of human immunoglobulin H-chain gene:

E. coli LE 392 strain (ATCC 33572) was infected with the gene library (an assembly of Charon 4A phages containing human chromosomal DNA) obtained in Example 2 to form a plaque. Clones containing human immunoglobulin gene were selected in accordance with the plaque hybridization method of Benton and Davis [see W. D. Benton and R. W. Davis, Science, 196, 180

(1977)] using a $^{32}$-P-labelled human immunoglobulin H-chain J gene. DNA was prepared from the Charon 4A phages containing human immunoglobulin gene by the method of Thomas and Davis [M. Thomas and R. W. Davis, J. Mol. Biol., 91, 315 (1974)].

EXAMPLE 4

Preparation of a restriction endonuclease cleavage map of human immunoglobulin gene:

One microgram of the Charon 4A DNA containing a human immunoglobulin gene obtained in Example 3 was dissolved in 20 microliters of a buffer for digestion with restriction endonucleases [50 mM Tris-HCl (pH 7.4)-100 mM NaCl-10 mM MgSO$_4$ aqueous solution for EcoRI, EcoRV, MluI or SphI; 10 mM Tris-HCl (pH 7.5)-60 mM NaCl-7 mM MgCl$_2$ aqueous solution for AatII, AvaI, BamHI, BstEII, HincII, HindIII, PstI or PvuII; 10 mM Tris-HCl (pH 7.4)-10 mM MgSO$_4$-1 mM dithiothreitol aqueous solution for BglII; and 10 mM Tris-HCl (pH 8.0)-20 mM KCl-7 mM MgCl$_2$-7 mM 2-mercaptoethanol solution for HpaI], and digested with two units of a restriction endonuclease (AatII was a product of Toyobo Ltd.; AvaI was a product of Bethesda Research Laboratories, Inc.; BstEII and SphI were products of New England Biolabs. Inc.; and the other endonucleases were products of Takara Shuzo Co., Ltd.) at 37° C. for more than 1 hour. Cleavage with BstEII was carried out at 60° C. for more than 1 hour. When the digestion was carried out by using two restriction endonucleases, there was used a procedure comprising first treating the DNA with one restriction endonuclease acting at a low salt concentration, then increasing the salt concentration to a predetermined concentration, and treating DNA with the other restriction endonuclease acting at a higher salt concentration.

After the digestion, 4 microliters of an aqueous solution containing 0.25% of bromophenol blue and 50% of glycerol, and the mixture was subjected to 0.8%-2.5% agarose gel electrophoresis. The agarose used was type II made by Sigma Co. designed for electrophoresis. A 40 mM Tris-CH$_3$COOH (pH 8.0)-1 mM EDTA aqueous solution was used as an electrophoresis running buffer. With a vertical gel having a thickness of 2 mm, the electrophoresis was carried out at a voltage of 6 to 9 V/cm for 1.5 to 3 hours. A product of digestion of λ phage DNA with HindIII (made by Boeling Manheim) was used as a molecular size marker for DNA fragments. After the electrophoresis, the DNA in the agarose gel was dyed with a 2 micrograms/ml aqueous solution of ethidium bromide, and by irradiating long wavelength ultraviolet light onto the gel, the digestion pattern was observed. By analyzing the patterns of digestion with the various restriction endonucleases either alone or in a combination of two, the relative positions of the restriction endonuclease cleavage sites were determined.

EXAMPLE 5

Recloning of a human immunoglobulin gene (a hybrid DNA of a 8.2 Kb HindIII fragment containing a human C$_{\gamma1}$ gene and E. coli plasmid pBR322):

Three micrograms of Charon 4A DNA containing a human immunoglobulin gene was digested with HindIII substantially in accordance with the method of Example 4, and subjected to agarose gel electrophoresis (gel concentration 0.8%). A band corresponding to DNA having a size of 8.2 kb and containing a C$_{\gamma1}$ gene was cut out and the agarose gel slice was dissolved in three times (vol/wt) its amount of an 8M aqueous NaClO$_4$ solution. A DNA fragment having a size of 8.2 kb was recovered from the agarose gel by the glass filter method of Chen and Thomas [C. W. Chen and C. A. Thomas Jr., Anal. Biochem. 101, 339 (1980)].

Separately, 1 microgram of E. coli plasmid pBR322 was digested with HindIII in accordance with Example 4, and reacted with 0.5 unit of alkaline phosphatase (E. coli C75) (a product of Takara Shuzo Co., Ltd.) at 45° C. for 1 hour. After the reaction, the reaction mixture was extracted with water saturated phenol three times in order to deactivate and remove the alkaline phosphatase in the reaction mixture.

The alkaline phosphatase treated product of the above digested pBR322 was mixed with an aqueous solution of the 8.2 kb HindIII fragment recovered from the agarose gel. The mixture was precipitated with ethanol, and the precipitate was dissolved in 50 microliters of a buffer for ligation (see Example 2). Two units of T4-DNA ligase was added, and the reaction was carried out at 11° C. for 12 hours to give a hybrid DNA.

E. coli C600 strain (ATCC 33525) was transformed with the hybrid DNA by an improved version of the usual CaCl$_2$ method [M. V. Norgard, K. Keen and J. J. Monaham, Gene. 3, 297 (1978)]. Specifically, E. coli C600 strain cultivated for 18 hours was inoculated in 5 ml of L-broth (1% tryptone, 0.5% yeast extract, 0.5% NaCl, pH 7.2) and grown to an extent corresponding to an optical density at 600 nm of 0.3. The cells were washed twice in a cold magnesium buffer [0.1M NaCl-5 mM MgCl$_2$-5 mM Tris-HCl (pH 7.6, 0° C.)], re-suspended in 2 ml of a cold calcium buffer [100 mM CaCl$_2$-250 mM KCl-5 mM MgCl$_2$-5 mM Tris-HCl (pH 7.6, 0° C.)], and left to stand at 0° C. for 25 minutes. The cells were then concentrated to one-tenth of their volume in a calcium buffer, and mixed with an aqueous solution of the hybrid DNA in a ratio of 2:1 (vol:vol). The mixture was maintained at 0° C. for 60 minutes, and after adding 1 ml of LBG-broth (1% tryptone, 0.5% yeast extract, 1% NaCl, 0.08% glucose, pH 7.2), cultivated at 37° C. for 1 hour. The culture fluid was inoculated in a selective medium (an L-broth plate containing 30 micrograms/ml of ampicillin) at a rate of 100 microliters/plate. The plate was cultivated overnight at 37° C. to grow the transformants. A DNA was prepared from the resulting colony by a known method, and by agarose gel electrophoresis, the existence of the desired hybrid DNA was determined.

RESTRICTION ENDONUCLEASE CLEAVAGE MAP OF SUBCLONES

In Examples 4 and 5, subclones having the restriction endonuclease cleavage maps shown in FIGS. 2 and 3 of the accompanying drawings were obtained.

FIG. 2 shows fragments obtained by cleaving a human chromosomal DNA containing an immunoglobulin gene with restriction endonuclease EcoRI. The 5'-terminal position is indicated as EcoRI-(1), and the 3'-terminal position, as EcoRI-(2). FIG. 2 also shows sites at which the DNA fragment can be cleaved with restriction endonuclease XbaI and XhoI. This fragment was cleaved with some restriction endonucleases and divided into several small fragments. Some fragments were inserted into the E. coli plasmid vector pBR322 to obtain four subclones shown in FIG. 3.

Subclone pTJ1B:

Obtained by inserting a small DNA fragment (about 8.2 kb) interposed between HindIII-(2) and HindIII-(3)

into the HindIII site of pBR322. The restriction endonuclease cleavage site map of this subclone is shown in FIG. 3, II-A. The presence of 3 to 4 Pst I sites were recognized between PstI-(3) and HindIII-(3) in FIG. 3, II-A.

Subclone pTJ1BR:

Obtained by insertion into pBR322 in the same way as in the preparation of pTJ1B above, but the orientation is reverse to that in pTJ1B. The restriction endonuclease cleavage map of this subclone is shown in FIG. 3, II-B.

Subclone pTJ5:

Obtained by inserting a small DNA fragment existing between PstI-(2) and PstI-(3) of the above subclone pTJ1B into the PstI site of pBR322. The restriction endonuclease cleavage map of this subclone is shown in FIG. 3, II-A-(1).

Subclone pTJ4:

Obtained by deleting from the above subclone pTJ1B a portion ranging from a Pst I site closest to Hind III-(3) existing between Hind III-(3) and Pst I-(3) to Pst I-(2). The restriction endonuclease cleavage map of this subclone is shown in FIG. 3, II-A-(2).

Subclone pTJ3: Obtained by inserting a small DNA fragment (about 3.4 kb) interposed between EcoRI-(1) and HindIII-(1) into a site between EcoRI and HindIII. A detailed restriction endonuclease cleavage map of this subclone is shown in FIG. 3, I.

EXAMPLE 6

Determination of the DNA sequences of the human immunoglobulin gene enhancer region:

The DNA sequences of the enhancer region and the V-D region of the H-chain of a human immunoglobulin gene were determined by the Maxam-Gilbert method [A. Maxam and W. Gilbert, Methods Enzymol., 65, 499 (1980)].

About 50 micrograms of the subclone pTJ3 DNA prepared in Example 5 was digested with BstEII in accordance with the method of Example 4. The resulting DNA fragment was dephosphorylated with alkaline phosphatase, and labelled with [$\gamma$-$^{32}$P] ATP using 5 units of polynucleotidekinase (produced by P-L Biochemicals Co.). The polynucleotidekinase reaction was carried out in a 50 mM Tris-HCl (pH 9.5)-10 mM MgCl$_2$-5 mM dithiothreitol aqueous solution, and [$\gamma$-$^{32}$P] ATP (made by Amersham Co.) was used in an amount corresponding to 100 micro Ci. The $^{32}$P-labelled DNA fragment was disgested with HpaI. The desired DNA fragment was separated by polyacrylamide gel electrophoresis (gel concentration 5%) and extracted from the gel. The resulting $^{32}$P-labelled BstEII/HpaI fragment was subjected to a partial hydrolysis reaction specific for each of the bases, and subjected to electrophoresis on polyacrylamide gel containing 7M urea (gel concentration 8% to 23%). The separated fragment was autoradiographed at −80° C. for 2 to 7 days, and the cleavage pattern was analyzed to obtain data for the determination of the DNA sequence of the enhancer region.

Thus, the DNA sequences including the enhancer DNA sequence of this invention shown in FIG. 4 were determined.

EXAMPLE 7

Determination of the DNA base sequence of a human immunoglobulin gene constant region:

The base sequence of the constant region of a human immunoglobulin gene was determined by the Maxam-Gilbert method [A. Maxam and W. Gilbert, Methods Enzymol., 65, 499 (1980)].

pTJ5 was digested with PstI, and labelled with [$\alpha$-$^{32}$P] ddATP using a 3'-terminal labelling kit (made by Amersham Co.). The $^{32}$P-labelled DNA fragment was digested with SmaI, and the desired DNA fragment was separated and recovered by polyacrylamide gel electrophoresis (gel concentration 5%). The resulting $^{32}$P-labelled PstI/SmaI DNA fragment was subjected to a partial hydrolysis reaction specific for each of the bases, and separated by electrophoresis on polyacrylamide gel containing 7M urea (gel concentration 8% to 23%). Then, the DNA fragment was autoradiographed at −80° C. for 2 to 7 days. The cleavage pattern was then analyzed to obtain data for the determination of the DNA sequence of the constant region as shown in FIG. 5.

EXAMPLE 8

Figures 6, 7:
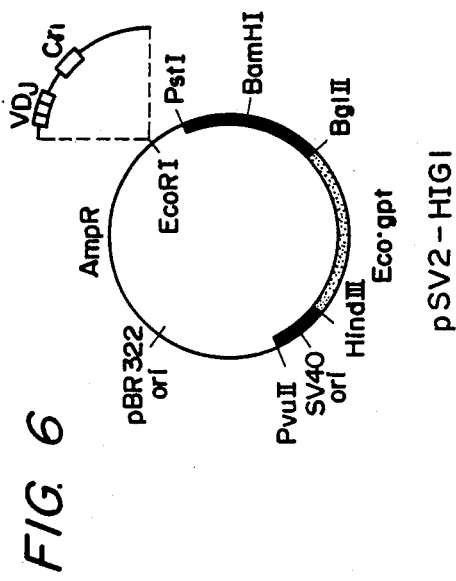

Construction of a human immunoglobulin gene expression plasmid:

An EcoRI fragment of the human H-chain gene (HIGl) obtained in Example 3, with a size of about 21 Kbp, was inserted into the EcoRI site of vector pSV-2gpt developed by P. Berg [R. C. Mulligan and P. Berg, Proc. Natl. Acad. Sci., U.S.A., 78, 2072 (1981)] to obtain a plasmid pSV2-HIG1 The restriction endonuclease cleavage map of this plasmid is shown in FIG. 6.

EXAMPLE 9

Isolation of a mouse chromosomal DNA:

Mouse hybridoma NL-1 cells (2×10$^7$) obtained from Dr. R. Ueda of Laboratory of Chemotherapy, Aichi Cancer Center Research Institute, Nagoya 464, Japan were treated with protease K in the presence of 1% SDS. Water-saturated phenol was then added to extract DNA. The aqueous layer was separated by centrifugation and dialyzed against 10 mM Tris-HCl buffer (pH 7.4) containing 0.1 mM NaCl and 0.1 mM EDTA (TNE) buffer. The aqueous solution was treated with ribonuclease A, and again extracted with water-saturated phenol. The aqueous layer was dialyzed against the TNE buffer to obtain 300 micrograms of mouse chromosomal DNA.

EXAMPLE 10

Preparation of a mouse gene library:

The mouse chromosomal DNA (150 micrograms) obtained in Example 9 was completely digested with restriction endonuclease EcoRI and subjected to agarose gel electrophoresis. A DNA fragment (5 micrograms) corresponding to 7 kb–9 kb was recovered from the agarose gel by electroelution.

The resulting DNA fragment (0.4 microgram) and Charon 4A vector EcoRI arms (Amersham Co.) were ligated by means of T4 DNA ligase, and packaged in vitro using a kit of Amersham Co. As a result, a mouse hybridoma NL-1 gene library (8×10$^6$ PFU/microgram) was obtained.

EXAMPLE 11

Screening of mouse immunoglobin H-chain gene:

E. Coli strain LE 392 was infected with the Charon 4A phage obtained in Example 10 containing DNA derived from mouse hybridoma NL-1 to form a plaque. Clones containing mouse antibody H-chain genes were screened by the plaque hybridization method using a $^{32}$P-labelled mouse immunoglobin H-chain J gene.

This procedure led to the isolation of a gene including all V regions (a 5' flanking region, VDJ regions and an enhancer region) of mouse hybridoma NL-1 having a size of 7.9 kb.

EXAMPLE 12

Preparation of a restriction endonuclease Cleavage map:

A 7.9 kb EcoRI fragment of the mouse hybridoma NL-1 H-chain DNA obtained in Example 11 was re-cloned into vector pBR322 and used to transform *E. Coli* strain DL-1 (ATCC 33849). The *E. Coli* strain was cultivated in large quantities to obtain about 1 mg of a plasmid (pBR-NL-1-H) having the 7.9 kb mouse hybridoma NL-1 H chain DNA fragment inserted into the EcoRI site of pBR322. The pBR NL-1-H was cleaved with restriction endonucleases, ECoRI, BamHI, HindIII, EcoRV and PvuII (Takara Shuzo Co., Ltd.) and SphI (Bethesda Research Laboratory), and a restriction endonuclease cleavage map was prepared as shown in FIG. 7. As a typical example, cleavage with EcoRI is shown below.

EXAMPLE 13

Determination of the DNA sequence of mouse immunoglobulin VDJ region:

The pBR-NL-1-H was cleaved with restriction endonucleases SpHI and PvuII to obtain two DNA fragments given by the inserted gene between SphI and PvuII sites. The DNA fragments were cloned into M13 phase vectors mp18 and mp19 (P. L. Biochemicals Co.) cleaved with SphI and HincII. DNA sequence determination was performed by the dideoxy chain termination method using an M13 sequencing kit (Takara Shuzo Co., Ltd.). The sequence of the SphI/PvuII fragment on the 5' side was determined both in the downstream direction from the SphI site and in the upstream direction from the PvuII site. The sequence of the SphI/PvuII fragment on the 3'side was determined in the downstream direction from the PvuII site. The DNA sequence of the variable region is shown in FIG. 8.

EXAMPLE 14

Construction of chimaeric immunoglobulin gene expression plasmid pMH-1:

The plasmid pBR-NL-1-H obtained by inserting an anti-human cALL immunoglobulin H-chain gene fragment (7.9 kb) into the EcoRI site of plasmid vector pBR322 was cleaved with restriction endonucleases EcoRV and BamHI. An EcoRV-BamHI fragment (about 2.7 kb) containing the entire mouse immunoglobulin H-chain variable region was separated by agarose gel electrophoresis and purified by the method of Example 3.

In the meantime, the plasmid vector pSV2-gpt mentioned hereinabove was cleaved with restriction endonucleases BamHI and HpaI, and a linear vector fragment having a size of about 5.3 kb and containing the Ecogpt gene was separated and purified (this vector gene is abbreviated as "fragment-1").

The EcoRV-BamHI fragment (about 2.7 kb) of pBR-NL-1-H obtained above was ligated with the BamI-HpaI fragment (about 5.3 kb) of pSV2-gpt mentioned above by using T4-DNA ligase. Subsequent cleavage with restriction endonuclease BamHI gave a linear DNA fragment (about 8.0 kb) containing about 2.7 kb of the variable region of NL-1-H. The DNA fragment was separated and purified (this DNA fragment gene is abbreviated as "fragment-2").

Furthermore, plasmid pSV-2-HIG1 containing a human immunoglobulin gene (about 21 kb) was cleaved with restriction endonuclease MluI to give a DNA fragment (about 17 kb) containing a human enhancer and $C_{\gamma 1}$, which was separated and purified. A BamHI linker (a product of Takara Shuzo Co., Ltd.) was ligated with the resulting gene fragment (about 17 kb) in accordance with the method of T. Maniatis et al. (T. Maniatis et al., "Molecular Cloning, Cold Spring Harbor Lab., 1982) to give a BamHI site to both ends (the resulting product is abbreviated as "fragment-4").

Figure 9:
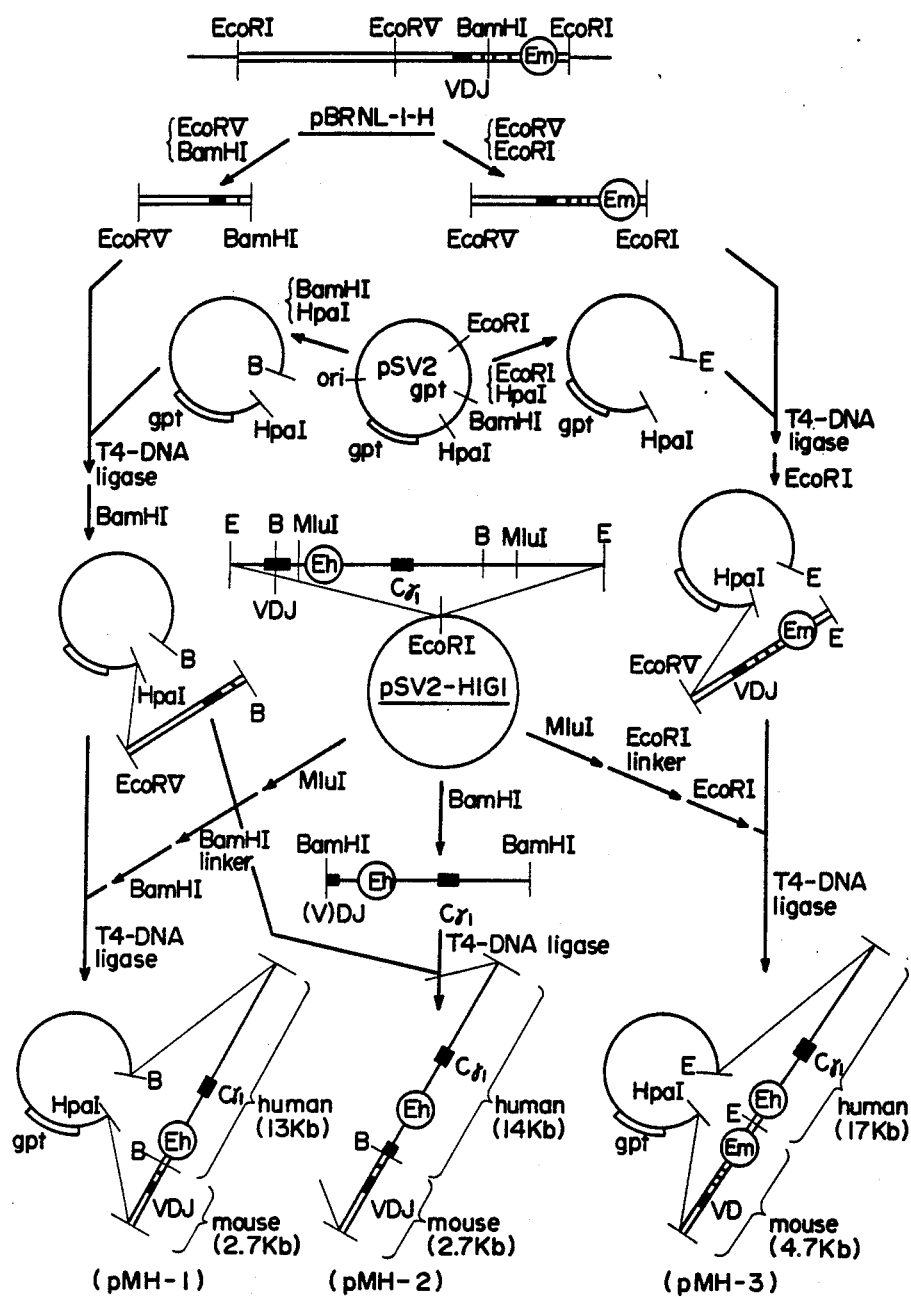

The fragment-4 was ligated with the fragment-2 by using T4-DNA ligase. *E. coli* strain MC1000 was transformed with the ligation product to obtain a chimaeric immunoglobulin gene in which the variable region of the mouse origin was joined to the constant region of the human origin through the human enhancer (Eh) (this gene is abbreviated as "pMH-1"). The flow chart for the preparation of the plasmid pMH-1 is shown in FIG. 9.

EXAMPLE 15

Construction of chimaeric immunoglobulin gene expression plasmid pMH-2:

Plasmid pSV-2-HIG1 containing a human immunoglobulin H-chain gene (about 21 kb) was cleaved with restriction endonuclease BamHI by a conventional method to give a fragment (about 14 kb) containing a human enhancer (Eh) and $C_{\gamma l}$. The resulting fragment was ligated with the fragment-2 by using T4-DNA ligase. *E. coli* MC1000 was transformed with the ligation product to give a chimaeric immunoglobulin gene in which the variable region was of the mouse origin and the constant region and the enhancer were of the human origin (this plasmid is abbreviated as "pMH-2"). The flow chart for the preparation of the plasmid pMH-1 is shown in FIG. 9.

EXAMPLE 16

Construction of chimaeric immunoglobulin gene expression plasmid pMH-3:

The plasmid pBR-NL-1-H was cleaved with restriction endonucleases EcoRV and EcoRI in the same way as in Example 3 to give a fragment (about 4.7 kb) containing the entire mouse immunoglobulin H-chain variable regions and the mouse enhancer (Em). Then, the vector pSV-2-gpt was cleaved with restriction endonucleases EcoRI and HpaI to give a fragment (about 4.7 kb) containing Ecogpt gene, which was separated and purified. The resulting fragment was ligated with the above mouse V gene fragment (about 4.7 kb) by using T4-DNA ligase, and the ligation product was then cleaved with restriction endonuclease EcoRI to give a linear DNA fragment (about 9.2 kb) containing the variable region (about 4.7 kb) of NL-1-H, which was separated and purified (this DNA fragment is abbreviated as "fragment-3").

Plasmid pSV2-HIG1 containing a human immunoglobulin H-chain gene (about 21 kb) was cleaved with restriction endonuclease MluI to give a fragment (about 17 kb) containing a human enhancer (Eh) and $C_{\gamma 1}$, which was separated and purified. An EcoRI linker (a product of Takara Shuzo Co., Ltd.) was ligated with the resulting fragment (about 17 kb) in accordance with the method of Maniatis et al. described in "Molecular Cloning" to give an EcoRI site to both ends (the resulting fragment is abbreviated as "fragment-5").

The fragment-5 was ligated with the fragment 3 by using T4-DNA ligase to give a chimaeric immunoglobulin gene having the human and mouse enhancers, a variable region of the mouse origin and a constant region of the human origin (this plasmid is abbreviated as "pMH-3").

The flow chart for the preparation of the plasmid pMH-3 is shown in FIG. 9.

EXAMPLE 17

Construction of a chimaeric immunoglobulin gene expression plasmid pMH-4:

The plasmid pBR-NL-1-H was cleaved with restriction endonucleases EcoRV and BamHI to give a fragment (about 2.7 kb) containing the entire V-gene segment of a mouse, which was separated and purified. EcoRI linker was ligated with the EcoRV terminus of this fragment to give an EcoRI site and form an EcoRI-BamHI fragment (about 2.7 kb).

In the meantime, the vector pSV2-gpt was cleaved with EcoRI and BamHI to give a linear vector fragment (4.6 kb) containing an Ecogpt gene, which was separated and purified. The resulting vector fragment was ligated with the above EcoRI-BamHi fragment (about 2.7 kb) by using T4-DNA ligase. The ligation product was then cleaved with restriction endonuclease BamHI to give a DNA fragment (about 7.3 kb) containing the variable region gene of NL-1-H (this DNA fragment is abbreviated as "fragment-6").

The fragment-6 was ligated with the fragment-4 obtained in Example 14 containing the human enhancer (Eh) and $C_{\gamma l}$ by using T4-DNA ligase. $E.\ coli$ MC1000 was transformed with the ligation product to give a chimaeric immunoglobulin gene having a variable region of the mouse origin and a constant region of the human origin joined through the human enhancer (Eh) (this plasmid is abbreviated as "pMH-4").

Figure 10:
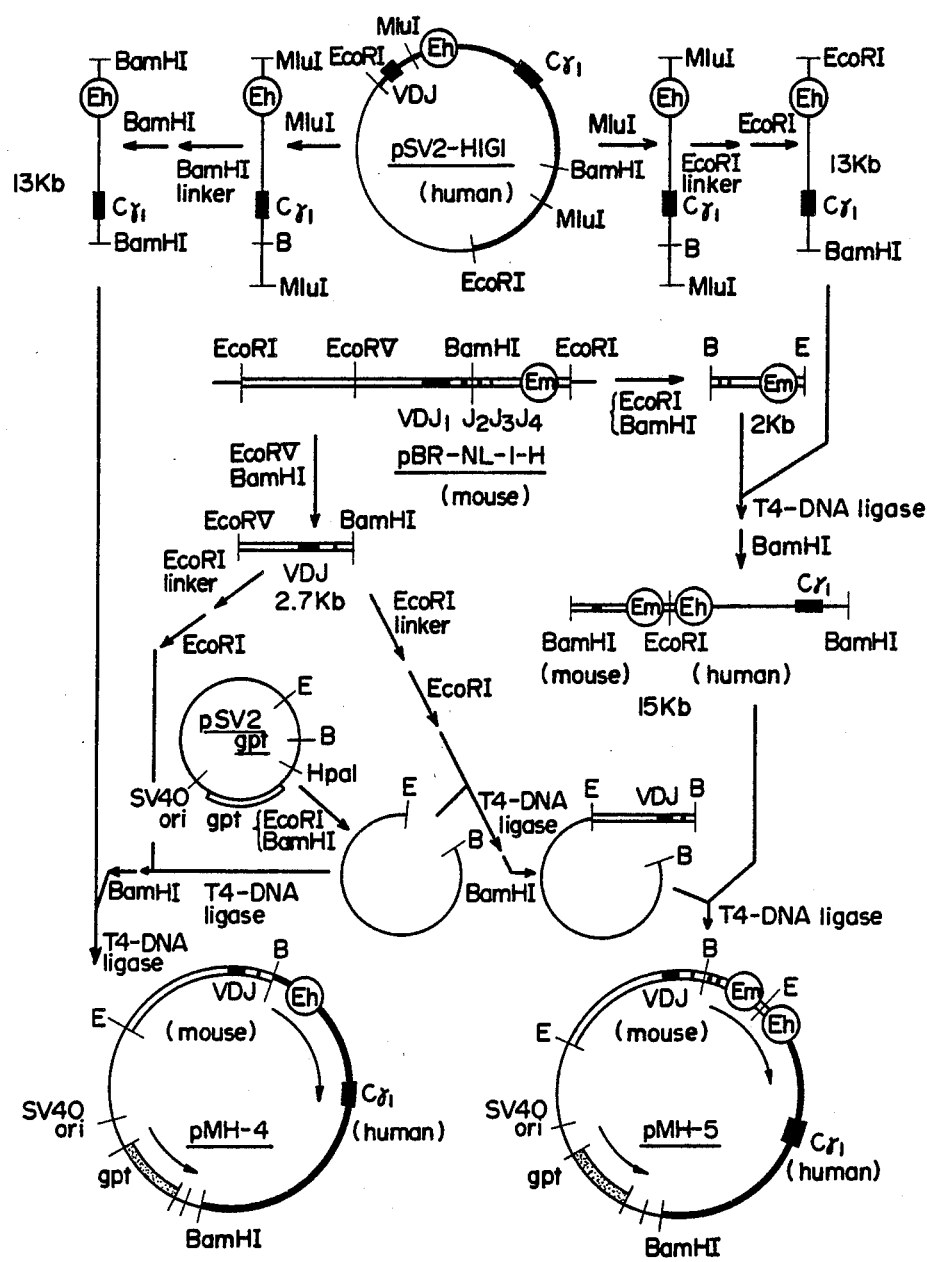

The flow chart for the preparation of the plasmid pMH-4 is shown in FIG. 10.

EXAMPLE 18

Construction of chimaeric immunoglobulin gene expression plasmid pMH-5:

The plasmid pBR-NL-1-H was cleaved with restriction endonucleases BamHI and EcoRI to obtain a fragment (about 2 kb) containing a mouse enhancer (Em), which was separated and purified. The fragment (about 2 kb) was ligated with the fragment-5 obtained in Example 16 by using T4-DNA ligase. The ligation product was cleaved with restriction endonuclease BamHI to give a BamHI fragment (about 13 kb) containing the mouse and human enhancers and human $C_{\gamma l}$. The BamHI fragment was ligated with the fragment-6 obtained in Example 17 by using T4-DNA ligase. $E.\ coli$ MC1000 was transformed with the ligation product to give a chimaeric immunoglobulin gene containing a variable region of the mouse origin and a constant region of the human origin joined through the mouse and human enhancers (this plasmid is abbreviated as "pMH-5").

The flow chart for the construction of the plasmid pMH-5 is shown in FIG. 10.

EXAMPLE 19

Expression of the chimaeric immunoglobulin genes:

Each of the chimaeric immunoglobulin gene expression plasmids pMH-1 to pMH-5 obtained in Examples 14 to 18 was introduced into $E.\ coli$ MC1000 in accordance with the method described in Example 5. The transformants were cultured in a medium containing ampicillin, and the plasmid was amplified by adding chloramphenicol. $E.\ coli$ protoplasts were obtained by treatment with lysozyme (Sigma Co.). The resulting protoplasts were fused with $2\times10^6$ mouse myeloma cells J558L or NS-1 in 50% PEG 4000 for 2 to 7 minutes. The fusion product was diluted with MEM medium (Gibco, Grand Island, N.Y.), and PEG 4000 was removed by centrifugation. The resulting cells were grown for 48 to 72 hours in RPMI 1640 complete medium (Gibco). The cell surfaces were then stained by fluorescence using FITC-labelled goat anti-human IgG (Cappel Laboratories, Inc.), and the expression of the chimaeric immunogloblin gene was checked. Strong expression was observed in the cells into which the expression plasmids pMH-1, pMH-2 and pMH-4 were introduced. On the other hand, relatively weak expession was observed in the cells into which the expression plasmids pMH-3 and pMH-5 were introduced.

RNA was extracted from the individual cells, and 20 micrograms of the resulting RNA was subjected to northern hybridization (T. Maniatis et al., Molecular Cloning, Cold Spring Harbor Lab., 1982) using a BamHI-PvuII fragment of plasmid pBR-NL-1-H containing mouse V, D, and J genes and a PstI(-(2)-PstI-(3) fragment of plasmid pSV2-HIGl containing part of human $C_{\gamma l}$ gene as probes. Strong hybridization was observed with RNAs of the cells in which the expression plasmids pMH-1, pMH-2 and pMH-4 were introduced, whereas hybridization was relatively weak with the RNAs of the cells in which the expression plasmids pMH-3 and pMH-5 were introduced.

In the present example, the degree of expression showed the same tendency in mouse myeloma J558L and NS-1.

The expression plasmid pMH-4 was introduced into mouse myeloma cells J558L by protoplast fusion and transferred to a selective medium containing 250 γ/ml xanthine, 15 γ/ml hypoxanthine and 6 γ/ml mycophenolic acid. The medium was exchanged for two successive days. Two weeks later, transformants having resistance to mycophenolic acid were obtained. mRNA was extracted from the transformants, and subjected to northern hybridization using a V-gene of a mouse VDJ and a human $C_{\gamma l}$ gene as a probe. At a size of 1.7 kb, a band was observed which corresponded to mRNA of a complete secretor H-chain.

The transformants were cultured in the presence of $^{35}$S-methionine (Amersham). The supernatant obtained was immunoprecipitated with anti-human IgG. The precipitate was subjected to polyacrylamide gel electrophoresis and fluorographed. It was determined that the chimaeric immunoglobulin H-chain protein was present in the form of $H_2L_2$ in the supernatant of the culture.

Southern hybridization was carried out in an attempt to detect the chimaeric immunoglobulin gene. This led to the determination that the chimaeric antibody gene existed in an average copy number of about 0.5 per cell.

What is claimed is:

1. A mouse-human chimaeric immunoglobulin heavy chain consisting essentially of a murine immunoglobulin heavy chain variable region which is derived from a murine immunoglobulin heavy chain which reacts specifically with human common acute lymphocytic leukemia antigen; and a human immunoglobulin G₁ heavy chain constant region, wherein the chimaeric immunoglobulin heavy chain has the following amino acid sequence:

Asp Val Gln Leu Val Glu Ser Gly Gly Gly Leu Val
Gln Pro Gly Gly Ser Arg Lys Leu Ser Cys Ala Ala
Ser Gly Phe Thr Phe Ser Ser Phe Gly Met His Trp
Val Arg Gln Ala Pro Glu Lys Gly Leu Glu Trp Val
Ala Tyr Ile Ser Gly Gly Ser Tyr Thr Ile Tyr Tyr
Ala Asp Thr Val Lys Gly Arg Phe Thr Ile Ser Arg
Asp Asn Pro Lys Asn Thr Leu Phe Leu Gln Met Thr
Ser Leu Arg Ser Glu Asp Thr Ala Met Tyr Tyr Cys
Ala Ser Ser Tyr Gly Asn Phe Trp Tyr Phe Asp Val
Trp Gly Ala Gly Thr Thr Val Thr Val Ser Ser
   Ala Ser Thr Lys
Gly Pro Ser Val Phe Pro Leu Ala Pro Ser Ser Lys
Ser Thr Ser Gly Gly Thr Ala Ala Leu Gly Cys Leu
Val Lys Asp Tyr Phe Pro Glu Pro Val Thr Val Ser
Trp Asn Ser Gly Ala Leu Thr Ser Gly Val His Thr
Phe Pro Ala Val Leu Gln Ser Ser Gly Leu Tyr Ser
Leu Ser Ser Val Val Thr Val Pro Ser Ser Ser Leu
Gly Thr Gln Thr Tyr Ile Cys Asn Val Asn His Lys
Pro Ser Asn Thr Lys Val Asp Lys Lys Val Glu Pro
Lys Ser Cys Asp Lys Thr His Thr Cys Pro Pro Cys
Pro Ala Pro Glu Leu Leu Gly Gly Pro Ser Val Phe
Leu Phe Pro Pro Lys Pro Lys Asp Thr Leu MET Ile
Ser Arg Thr Pro Glu Val Thr Cys Val Val Val Asp
Val Ser His Glu Asp Pro Glu Val Lys Phe Asn Trp
Tyr Val Asp Gly Val Glu His Asn Ala Lys Thr
Lys Pro Arg Glu Glu Gln Tyr Asn Ser Thr Tyr Arg
Val Val Ser Val Leu Thr Val Leu His Gln Asp Trp
Leu Asn Gly Lys Glu Tyr Lys Cys Lys Val Ser Asn
Lys Ala Leu Pro Ala Pro Ile Glu Lys Thr Ile Ser
Lys Ala Lys Gly Gln Pro Arg Glu Pro Gln Val Tyr
Thr Leu Pro Pro Ser Arg Glu Glu MET Thr Lys Asn
Gln Val Ser Leu Thr Cys Leu Val Lys Gly Phe Thr
Pro Ser Asp Ile Ala Val Glu Trp Glu Ser Asn Gly
Gln Pro Glu Asn Asn Tyr Lys Thr Thr Pro Pro Val
Leu Asp Ser Asp Gly Ser Phe Phe Leu Tyr Ser Lys
Leu Thr Val Asp Lys Ser Arg Trp Gln Gln Gly Asn
Val Phe Ser Cys Ser Val MET His Glu Ala Leu His
Asn His Tyr Thr Gln Lys Ser Leu Ser Leu Ser Pro
Gly Lys. -.

* * * * *